US009675391B2

(12) United States Patent
Roman et al.

(10) Patent No.: US 9,675,391 B2
(45) Date of Patent: Jun. 13, 2017

(54) HAMMERTOE IMPLANT WITH ENHANCED GRIPPING SURFACES

(71) Applicant: ARROWHEAD MEDICAL DEVICE TECHNOLOGIES LLC, Collierville, TN (US)

(72) Inventors: Scott R. Roman, Hampton, GA (US); Thomas J. Twardzik, Germantown, TN (US)

( * ) Notice: Subject to any disclaimer, the term of this patent is extended or adjusted under 35 U.S.C. 154(b) by 0 days.

(21) Appl. No.: 14/776,066

(22) PCT Filed: Mar. 12, 2014

(86) PCT No.: PCT/US2014/024485
§ 371 (c)(1),
(2) Date: Sep. 14, 2015

(87) PCT Pub. No.: WO2014/165123
PCT Pub. Date: Oct. 9, 2014

(65) Prior Publication Data
US 2016/0030096 A1 Feb. 4, 2016

Related U.S. Application Data

(60) Provisional application No. 61/780,360, filed on Mar. 13, 2013.

(51) Int. Cl.
*A61B 17/72* (2006.01)
*A61F 2/42* (2006.01)
*A61B 17/00* (2006.01)

(52) U.S. Cl.
CPC ...... *A61B 17/7291* (2013.01); *A61B 17/7233* (2013.01); *A61B 17/7283* (2013.01);
(Continued)

(58) Field of Classification Search
CPC .................................................. A61B 17/7291
See application file for complete search history.

(56) References Cited

U.S. PATENT DOCUMENTS

2004/0220574 A1* 11/2004 Pelo ...................... A61F 2/0063
606/232
2006/0129153 A1   6/2006 Klaue et al.
(Continued)

OTHER PUBLICATIONS

International Search Report for PCT/US2014/024485 dated Jul. 10, 2014.
(Continued)

*Primary Examiner* — Nicholas Plionis
(74) *Attorney, Agent, or Firm* — Heslin Rothenberg Farley & Mesiti P.C.; John W. Boger, Esq.

(57) ABSTRACT

An intramedullary fixation device used in bone fixation and stabilization on a patient includes a longitudinally extending rigid body, a distal head disposed at a distal end of the body and sized for insertion into an intramedullary canal of a phalanx of the patient, the distal head having a central core portion and a plurality of extending distal wings radially projecting from the central core portion. A proximal head at a proximal end of the body is sized for insertion into an intramedullary canal of a phalanx of the patient. It has a central core portion and a plurality of proximal wings extending radially outwardly from the central core portion.

5 Claims, 12 Drawing Sheets

(52) U.S. Cl.
CPC .. *A61F 2/4225* (2013.01); *A61B 2017/00831* (2013.01); *A61B 2017/00982* (2013.01); *A61F 2002/4233* (2013.01)

(56) References Cited

U.S. PATENT DOCUMENTS

| | | | |
|---|---|---|---|
| 2007/0083202 A1* | 4/2007 | Eli Running | A61B 17/72 606/62 |
| 2008/0132894 A1* | 6/2008 | Coilard-Lavirotte | A61B 17/1604 606/60 |
| 2009/0005782 A1* | 1/2009 | Chirico | A61B 17/1617 606/63 |
| 2009/0036893 A1 | 2/2009 | Kartalian et al. | |
| 2010/0324556 A1 | 12/2010 | Tyber et al. | |
| 2011/0172668 A1 | 7/2011 | Frake | |
| 2011/0257652 A1 | 10/2011 | Roman | |
| 2011/0276099 A1* | 11/2011 | Champagne | A61B 17/7225 606/328 |
| 2011/0301652 A1 | 12/2011 | Reed et al. | |

OTHER PUBLICATIONS

Extended European Search Report issued in European Patent Application 14780322.5 mailed on Nov. 16, 2016.

* cited by examiner

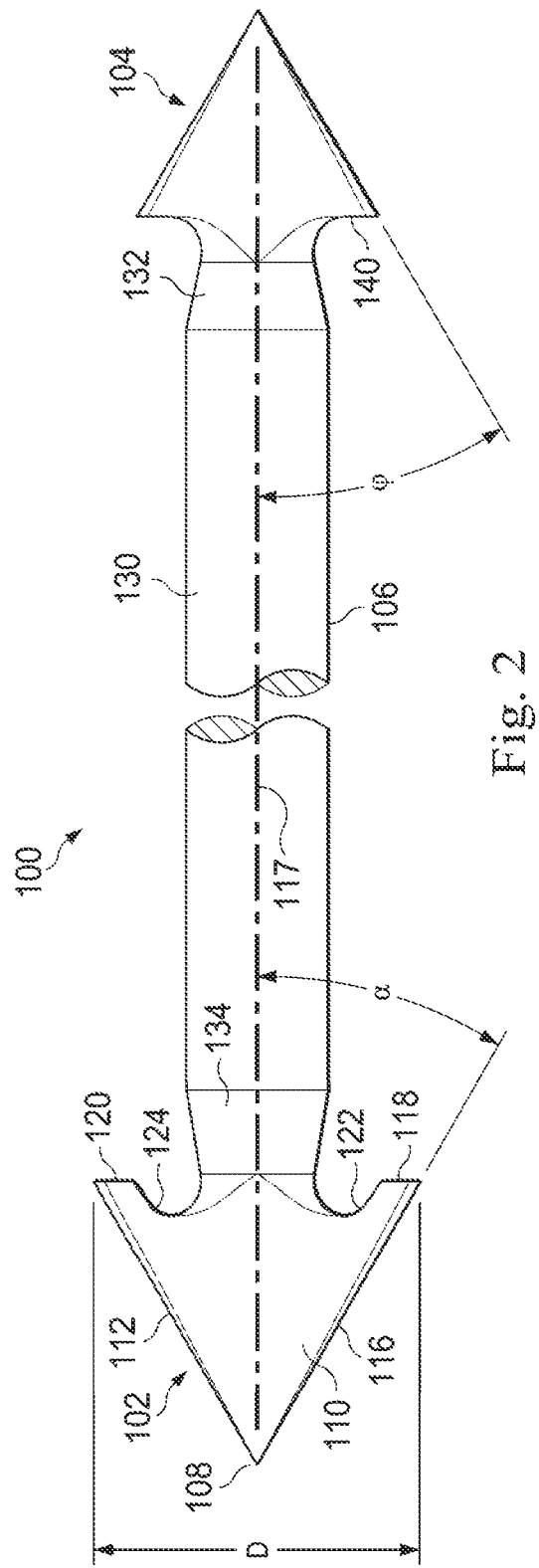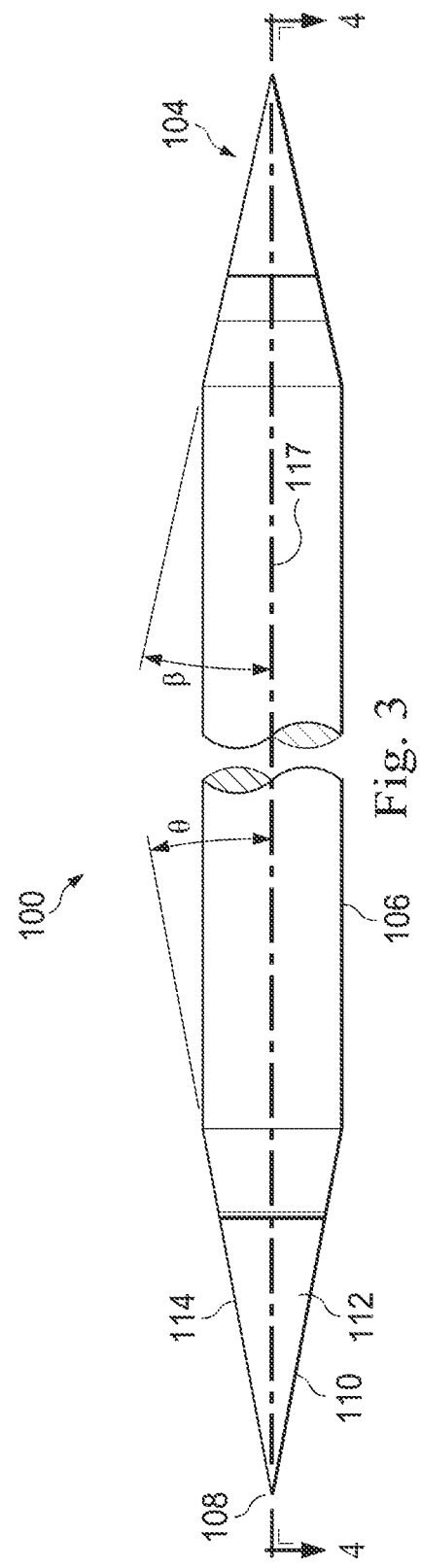

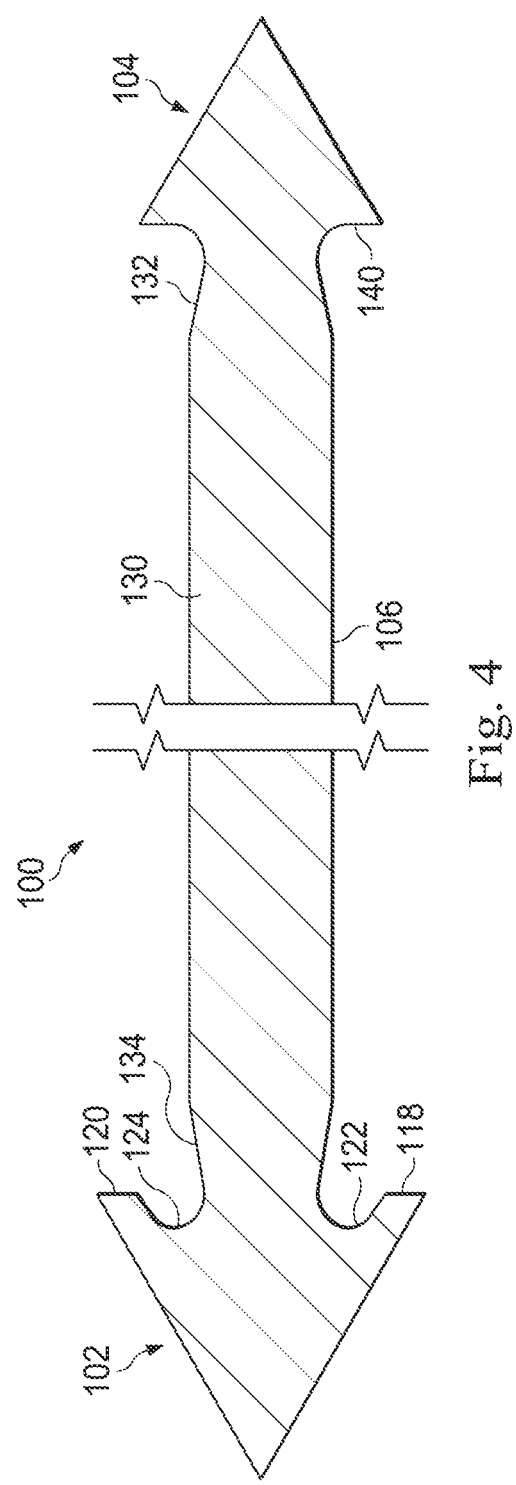

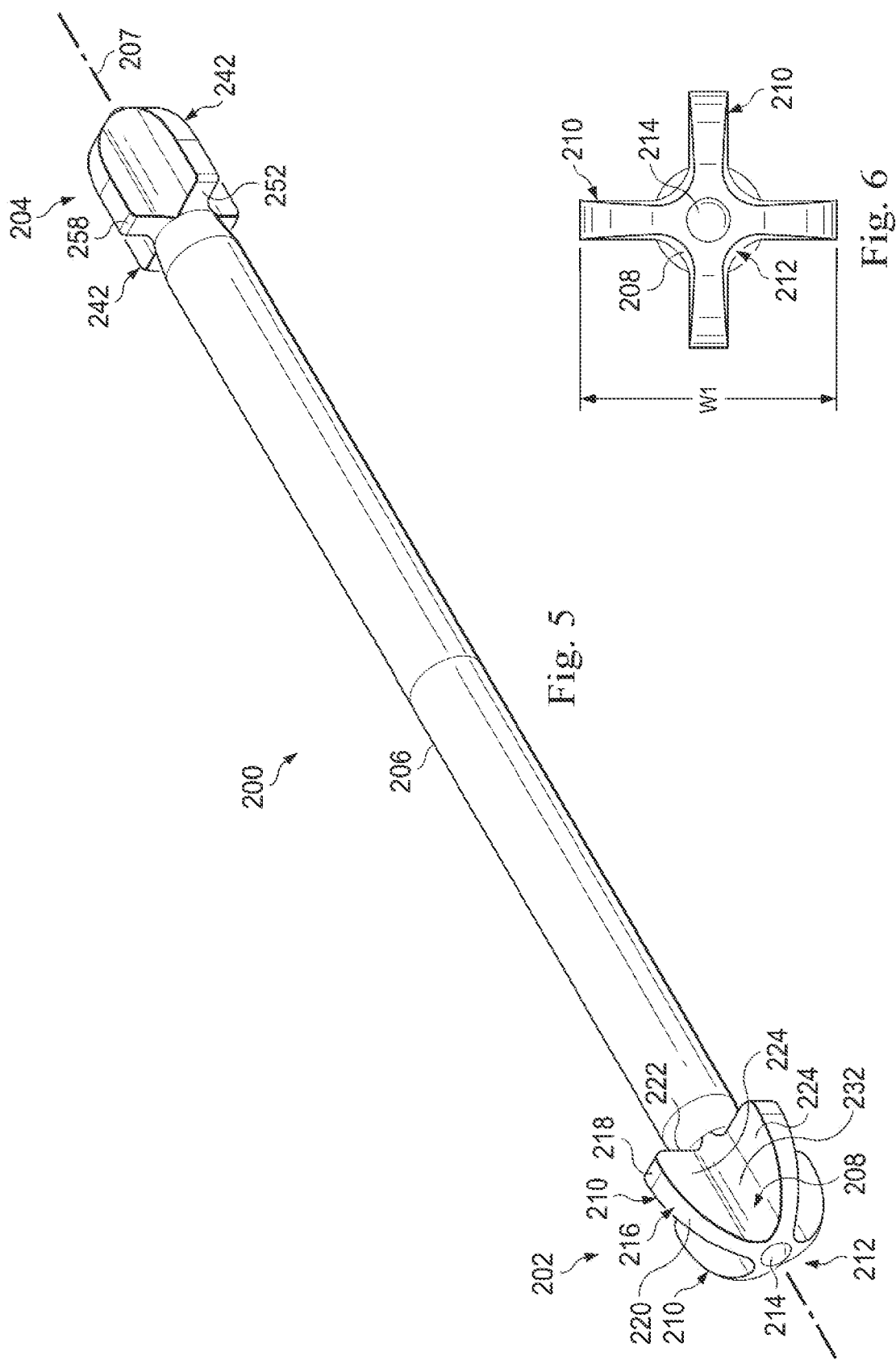

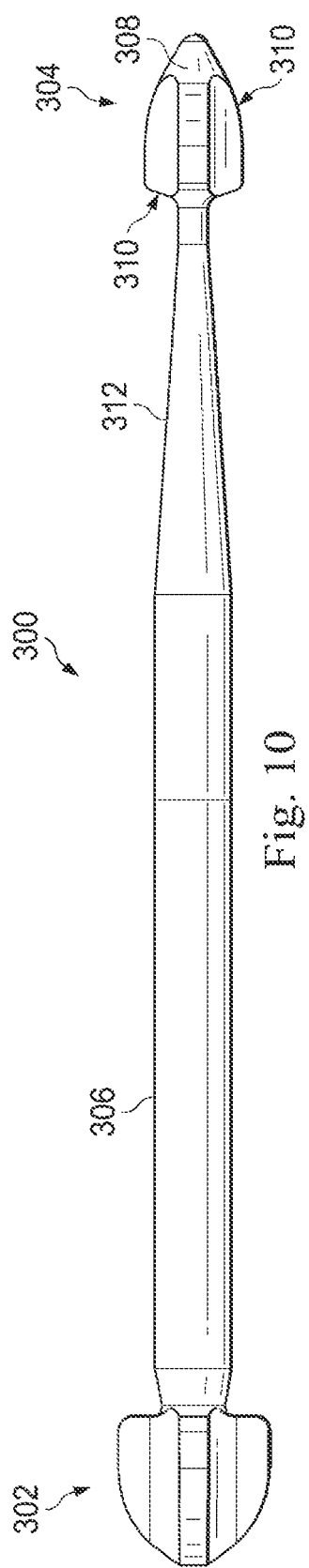
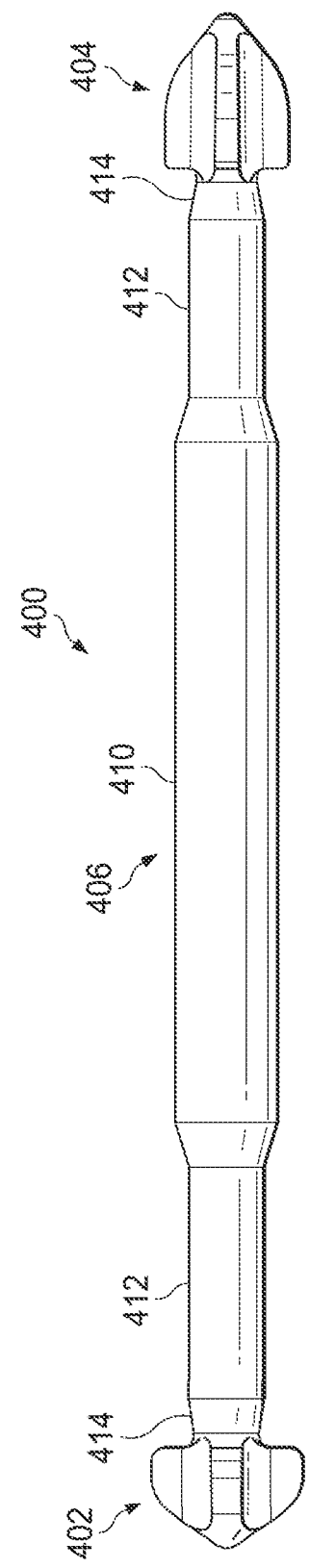

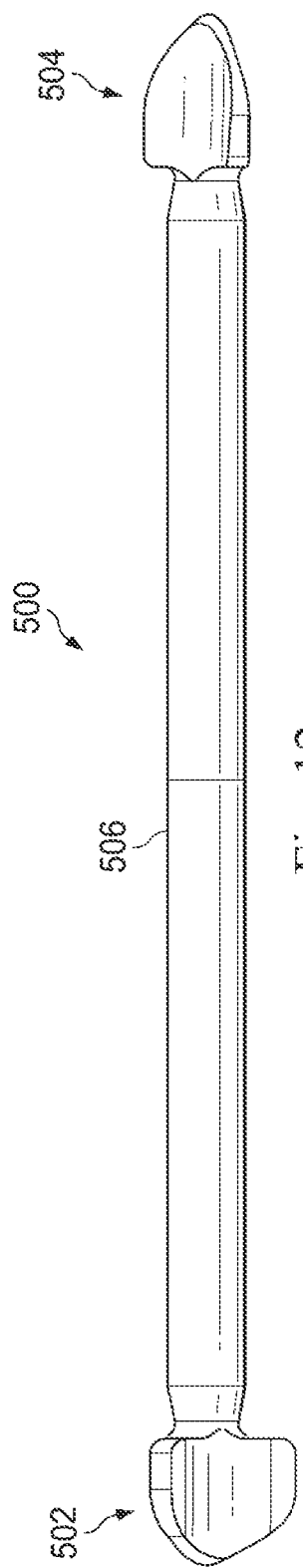
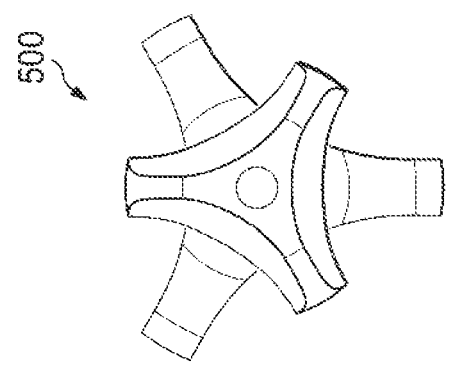
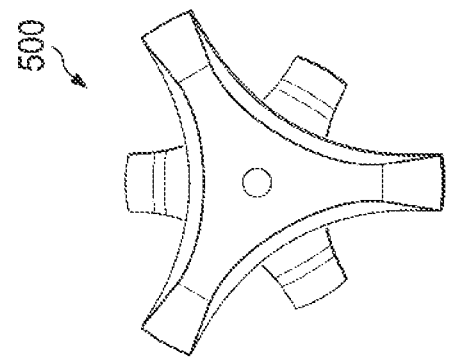
Fig. 12
Fig. 13
Fig. 14

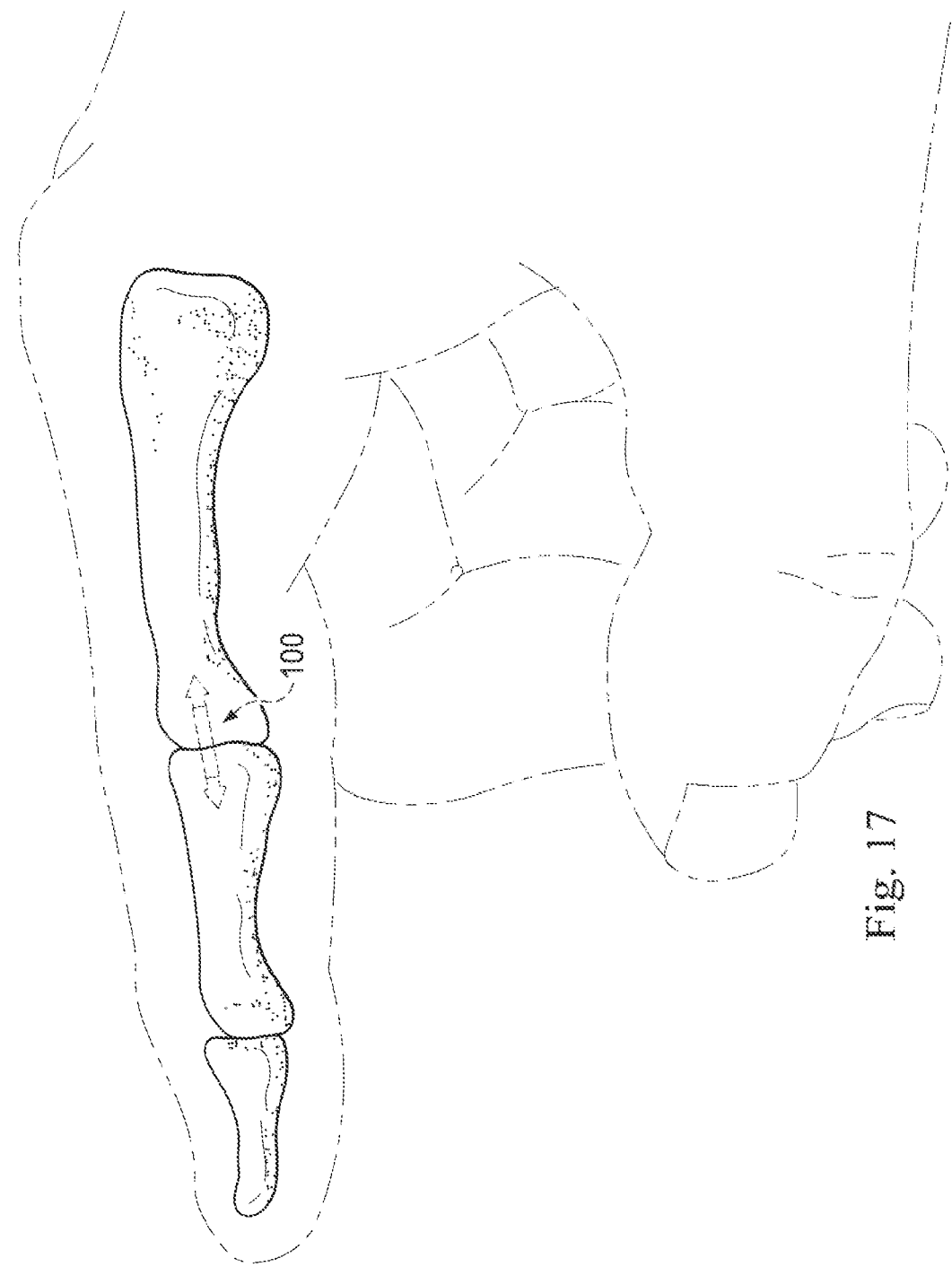

HAMMERTOE IMPLANT WITH ENHANCED GRIPPING SURFACES

CROSS-REFERENCE TO RELATED APPLICATIONS

This application is a National Stage application based on International Application No. PCT/US2014/024485 filed on Mar. 12, 2014, published as WO2014/165123 A1on Oct. 9, 2014, which claims priority benefit under 35 U.S.C. §119(e) of U.S. provisional application No. 61/780,360 filed on Mar. 13, 2013. These applications, along with U.S. application Ser. No. 14/206,171 filed on Mar. 12, 2014, are incorporated herein by reference in their entireties.

BACKGROUND

Hammertoe deformities occur when the metatarsophalangeal joint between phalanges in a toe are cocked upward and the proximal interphalangeal joint bends downward. This deformity can become quite painful and can limit the ability of a person with hammertoe to walk and perform other daily activities. Hammertoe may be caused by any number of factors, including heredity, the long-term use of poorly fitting shoes, having a long second toe, hallux valgus pressing against the second toe, connective tissue disorders and trauma.

While some minor cases may be treated with non-surgical remedies, surgeries are often necessary to provide real correction and pain relief. Some surgical methods include stabilizing the toes using a smooth K-wire placed in an antegrade manner through the middle and distal phalanges while joint extension and distraction are maintained. The K-wire may then be placed in retrograde fashion into the proximal phalanx while joint extension and distraction are maintained. Fixation lasts for 4-6 weeks after surgery. During that time, the pins are capped so that the sharp ends do not catch on objects, such as bed sheets. Even with this form of fixation, non-unions, K-wire migration, and loss of fixation can be quite common. Further, the external K-wires may lead to pin tract infections or movement of bone along the smooth wire, including rotation of the distal aspect of the toe. These types of challenges make alternative fixation methods desirable.

The system and methods disclosed herein overcome one or more of the deficiencies of the prior art.

SUMMARY

In one exemplary aspect, the present disclosure is directed to an intramedullary fixation device used in bone fixation and stabilization on a patient. The device includes a longitudinally extending rigid body and a distal head disposed at a distal end of the body. The distal head is sized for insertion into an intramedullary canal of a phalanx of the patient. The distal head has a central core portion and a plurality of extending distal wings radially projecting from the central core portion. A proximal head at a proximal end of the body is sized for insertion into an intramedullary canal of a phalanx of the patient. It has a central core portion and a plurality of proximal wings extending radially outwardly from the central core portion.

In an exemplary aspect, the present disclosure is directed to an intramedullary fixation device used in bone fixation and stabilization. The device includes an arrowhead-shaped distal head comprising a distal end having a distal tip, with the distal head having first, second, third, and fourth outwardly facing side surfaces forming a pyramidal shape. The first and third side surfaces may be opposed from each other and form a first angle, and the second and fourth side surfaces may be opposed from each other and form a second angle. The second angle is different than the first angle. Each of the first and third side surfaces have a proximally projecting edge forming a tip of a barb, where the barbs are configured to engage tissue and inhibit rotational movement and inhibit axial movement of the distal head in a proximal direction. The distal head has a first dimensional width measured between proximally projecting edges of the first and third side surfaces. The device also includes an arrowhead-shaped proximal head comprising a proximal end having a proximal tip. The proximal head has fifth, sixth, seventh, and eighth outwardly facing side surfaces. The fifth and seventh side surfaces may be opposed from each other and form a third angle, and the sixth and eighth side surfaces may be opposed from each other and form a fourth angle. The third angle is different than the fourth angle. Each of the fifth and seventh side surfaces has a distally projecting edge. The proximal head includes a trailing edge surface intersecting the distally projecting edge of the fifth and seventh side surfaces, with the trailing edge surface extending in a direction substantially perpendicular to a longitudinal direction of the proximal head and intersecting with a neck region. The proximal head has a second dimensional width measured between distally projecting edges of the fifth and seventh side surfaces, with the second dimensional width being within the range of about 1.3-1.5 times the first dimensional width. A rigid body extends between and connects the distal head and the proximal head. The rigid body has a neck region joined to the trailing edge surface of the proximal head in a manner that the trailing edge surface is perpendicular to a longitudinal axis of the body. The body has a rigidity sufficient to withstand bending loading applied by the phalanges.

In an aspect, the first angle is smaller than the third angle. In an aspect, the first angle is smaller than the second angle and the third angle is smaller than the fourth angle. In an aspect, the second and fourth side surfaces include proximal ends that relatively smoothly transition to the body. In an aspect, the distal head comprises a first undercut and a second undercut, the first and second undercuts respectively cooperating with the first and third side surfaces to form the barbs, each of the first and second undercuts having a depth such that the barb tips are disposed proximal of the respective undercut. In an aspect, the body comprises a main portion, a distal neck portion, and a proximal neck portion, the distal and proximal neck portions having a cross-sectional area smaller than a cross-section area of the main portion.

In an exemplary aspect, the present disclosure is directed to an intramedullary fixation device used in bone fixation and stabilization on a patient that includes a longitudinally extending rigid body having a rigidity sufficient to withstand bending loading applied by the phalanges, with the rigid body having a longitudinal axis extending through at least a portion of the body. A distal head is disposed at a distal end of the body and sized for insertion into an intramedullary canal of a phalanx of the patient. The distal head has a central core portion and a plurality of extending distal wings radially projecting from the central core portion. Each distal wing comprises an outer surface portion having an outer perimeter surface portion and a curved leading surface portion. The curved leading surface portion curves from the outer perimeter surface portion and smoothly intersects at the central core portion of the distal head. Each wing of the distal head also comprises a proximally facing trailing surface portion substantially perpendicular to the longitudinal axis of the rigid body. The distal head has a first maximum diameter defined by the outer perimeter surface portion of the distal wings and a first wing length. The device also includes a proximal head at a proximal end of the body sized for insertion into an intramedullary canal of a phalanx of the patient. The proximal head has a central core portion and a plurality of proximal wings extending radially outwardly from the central core portion. Each proximal wing comprises an outer surface portion having an outer perimeter surface portion and a curved leading surface portion. The curved leading surface portion curves from the outer perimeter surface portion and smoothly intersects at the central core portion of the proximal head. Each proximal wing also comprises a distally facing trailing surface portion substantially perpendicular to the longitudinal axis of the rigid body. The proximal head has a second maximum diameter defined by the outer perimeter surface portion of the distal wings and a second wing length, wherein the first maximum diameter of the distal wings is less than the second maximum diameter of the proximal wings, and wherein first wing length of the distal wings is greater than the second wing length of the proximal wings.

In an aspect, at least one of the proximal wings is wedge-shaped, such that the trailing surface portion has a thickness greater than at the curved leading surface portion. In an aspect, the body includes a central region and end regions, with the central region having a cross-section width greater than the cross-sectional width of the end regions. In an aspect, the central region extends between about 40 and 70% of the length of the body. In an aspect, the body comprises a narrow region adjacent one of the proximal and distal heads, the narrow region extending from said one of the proximal and distal heads more than 20% of the length of the body. In an aspect, the narrow region is adjacent the proximal head. In an aspect, the distal head comprises a leading nub disposed on the distal end of the distal head. In an aspect, the device comprises a fixation-promoting coating disposed on the body. In an aspect, the body includes a plantar grade bend in a range of about 5 to 15 degrees. In an aspect, the central core has a cross-sectional size smaller than a cross-sectional size of the body. In an aspect, the body is formed of two rigid elements joined together. In an aspect, the device has an overall length, and the proximal and distal heads form not more than about 30% of the overall length. In an aspect, the central core portion on the distal head smoothly connects adjacent wings without edges or corners. In an aspect, the wings form a cruciate or plus shape when viewed from an end. In an aspect, the device comprises more than four distal wings and more than four proximal wings. In an aspect, the plurality of distal wings is symmetrically disposed about the distal head and wherein the plurality of proximal wings is symmetrically disposed about the proximal head.

In yet another exemplary aspect, the present disclosure is directed to an intramedullary fixation device used in bone fixation and stabilization on a patient that includes a longitudinally extending rigid body having a rigidity sufficient to withstand bending loading applied by the phalanges, with the rigid body having a longitudinal axis extending through at a least a portion of the body. The device also includes a distal head disposed at a distal end of the body and sized for insertion into an intramedullary canal of a phalanx of the patient. The distal head has a central core portion and a plurality of extending distal wings radially projecting from the central core portion. The central core portion has an outer surface smoothly intersecting with the adjacent distal wings and including a leading nub. Each distal wing comprises an outer surface portion having an outer perimeter surface portion and a curved leading surface portion, where the curved leading surface portion curves from the outer perimeter surface portion and smoothly intersects at the central core portion of the distal head. Each wing of the distal head also comprises a proximally facing trailing surface portion substantially perpendicular to the longitudinal axis of the rigid body. The distal head has a first maximum diameter defined by the outer perimeter surface portion of the distal wings and a first wing length. The device also includes a proximal head at a proximal end of the body sized for insertion into an intramedullary canal of a phalanx of the patient. The proximal head has central core portion and a plurality of proximal wings extending radially outwardly from the central core portion. The central core portion has an outer surface smoothly intersecting with the adjacent distal wings and including a leading nub. Each proximal wing comprises an outer surface portion having an outer perimeter surface portion and a curved leading surface portion, where the curved leading surface portion curves from the outer perimeter surface portion and smoothly intersects at the central core portion of the proximal head. Each proximal wing also comprises a distally facing trailing surface portion substantially perpendicular to the longitudinal axis of the rigid body. The proximal head has a second maximum diameter defined by the outer perimeter surface portion of the distal wings and a second wing length, wherein the first maximum diameter of the distal wings is less than the second maximum diameter of the proximal wings, and wherein first wing length of the distal wings is greater than the second wing length of the proximal wings, wherein the device has an overall length, and the proximal and distal heads form not more than about 25% of the overall length.

In an aspect, at least one of the proximal wings and is wedge-shaped, such that the trailing surface portion has a thickness greater than at the curved leading surface portion. In an aspect, the body includes a central region and end regions, with the central region having a cross-section width greater than the cross-sectional width of the end regions. In an aspect, the central region extends between about 40% and 70% of the length of the body. In an aspect, the body comprises a narrow region adjacent one of the proximal and distal heads, the narrow region extending from said one of the proximal and distal heads more than 20% of the length of the body. In an aspect, the narrow region is adjacent the proximal head.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 2 is an illustration of the exemplary intramedullary fixation device of FIG. 1 in accordance with one aspect of the present disclosure.

FIG. 3 is an illustration of a side view of the exemplary intramedullary fixation device of FIG. 2 in accordance with one aspect of the present disclosure.

FIG. 4 is an illustration of a cross-sectional view of the exemplary intramedullary fixation device of FIG. 3 along the lines 4-4 in FIG. 3 in accordance with one aspect of the present disclosure.

FIGS. 5-9 are illustrations of another exemplary intramedullary fixation device in accordance with one aspect of the present disclosure.

FIG. 10 is an illustration of another exemplary intramedullary fixation device in accordance with one aspect of the present disclosure.

FIG. 11 is illustrations of another exemplary intramedullary fixation device in accordance with one aspect of the present disclosure.

FIGS. 12-16 are illustrations of another exemplary intramedullary fixation device in accordance with one aspect of the present disclosure.

FIG. 17 is an illustration of an exemplary intramedullary fixation device disposed between and within adjacent phalanges of a hand of a patient in accordance with one aspect of the present disclosure.

DETAILED DESCRIPTION

Figure 1:
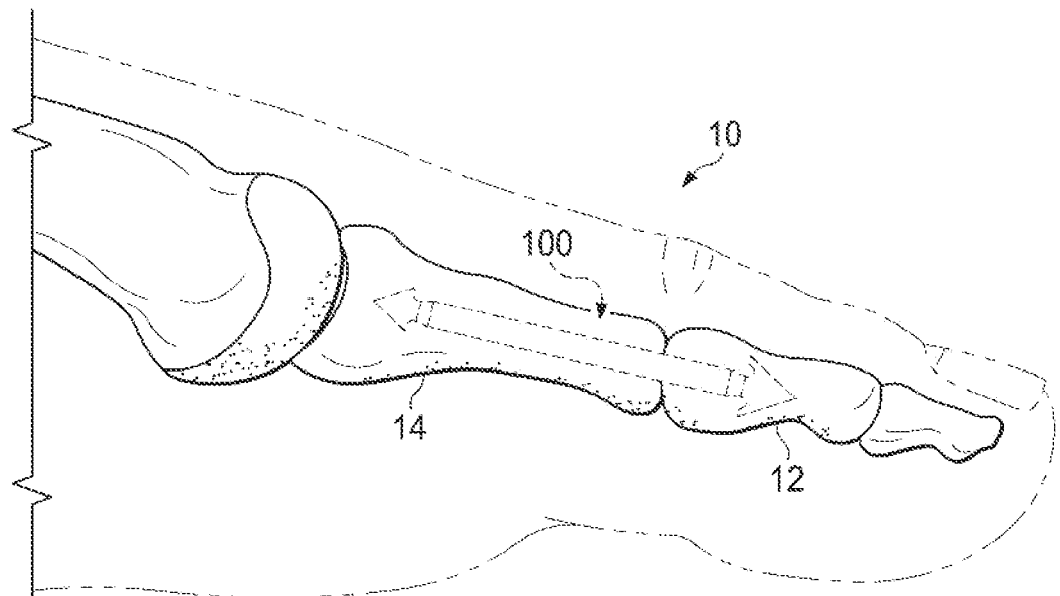
FIG. 1 is an illustration of an exemplary intramedullary fixation device disposed between and within adjacent phalanges of a toe of a patient in accordance with one aspect of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to intramedullary systems, methods, and devices used for bone fixation and stabilization of toes and fingers across fusion or fracture sites, and treat deformities, including for example, hammertoe deformities. The intramedullary fixation device includes unique arrow designs on both its proximal and distal ends, and in some embodiments, with the arrow designs varying in size and shape. It is arranged to be completely intramedullary when implanted with no parts of the device exposed outside the skin. Further, it is arranged to resist the rotational and pull-out forces affecting the lesser toes. Its particular design shape may help it maintain the initial compression applied at insertion.

FIG. 1 shows an exemplary toe 10 having an intermediate phalanx 12 and a proximal phalanx 14. In this example, the toe 10 has been surgically treated to correct a deformity such as hammertoe as discussed above. Accordingly, the toe includes an implanted intramedullary fixation device 100 disposed therein in accordance with an exemplary aspect of the present disclosure. In this example, the device 100 extends between and is implanted within the intermediate and proximal phalanges 12, 14.

Figure 1A:
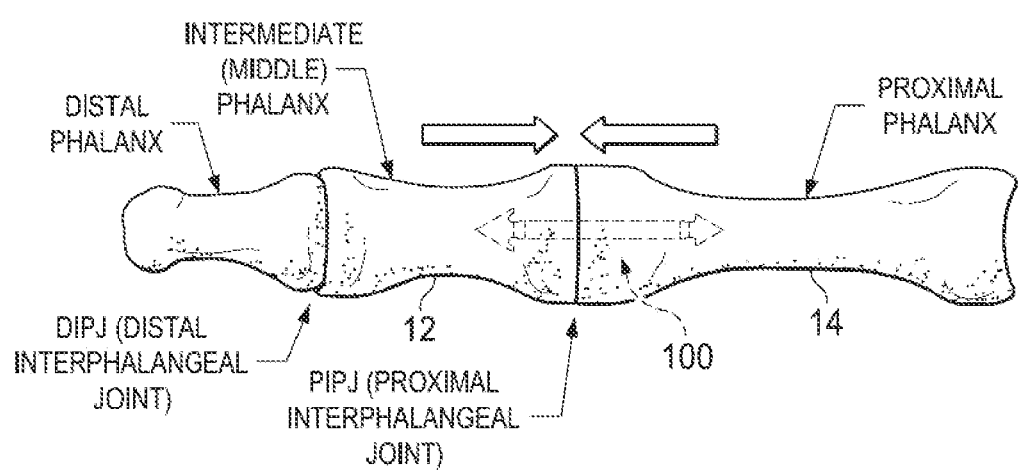
FIGS. 1A-1D are illustrations of exemplary intramedullary fixation devices disposed between and within adjacent phalanges of a toe of a patient in accordance with different aspects of the present disclosure.
Figure 1B:
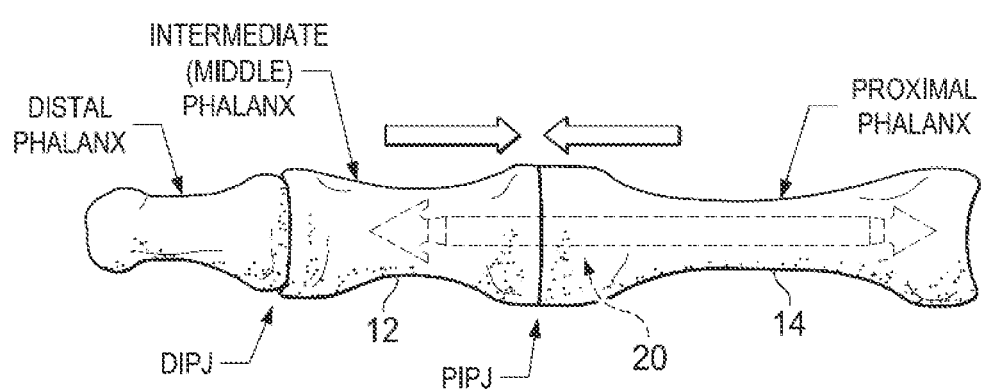

FIG. 1A shows the exemplary device 100 in greater detail configured and disposed to anchor in the cortex of the proximal phalanx and the intermediate phalanx. FIG. 1B shows an exemplary device 20 configured and disposed to anchor in the subchondral bone of the proximal phalanx and in the intermediate phalanx.

Figure 1C:
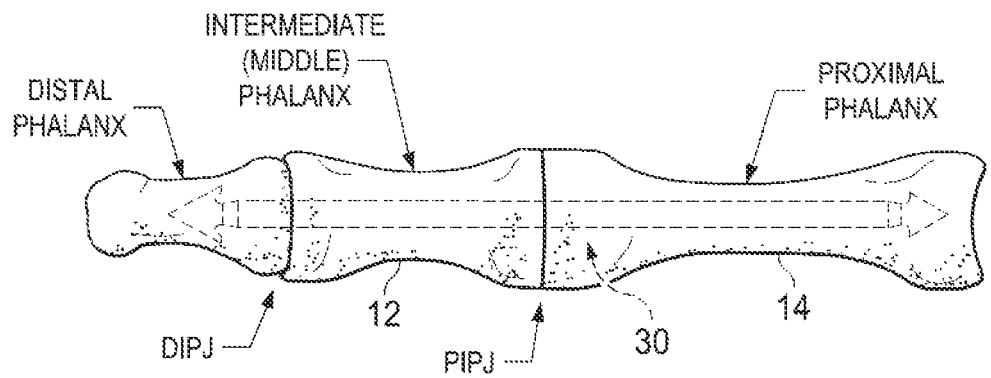

FIG. 1C shows an exemplary device 30 configured and disposed to anchor in the subchondral bone of the proximal phalanx, to entirely pass through the intermediate phalanx, and to anchor in the distal phalanx.

Figure 1D:
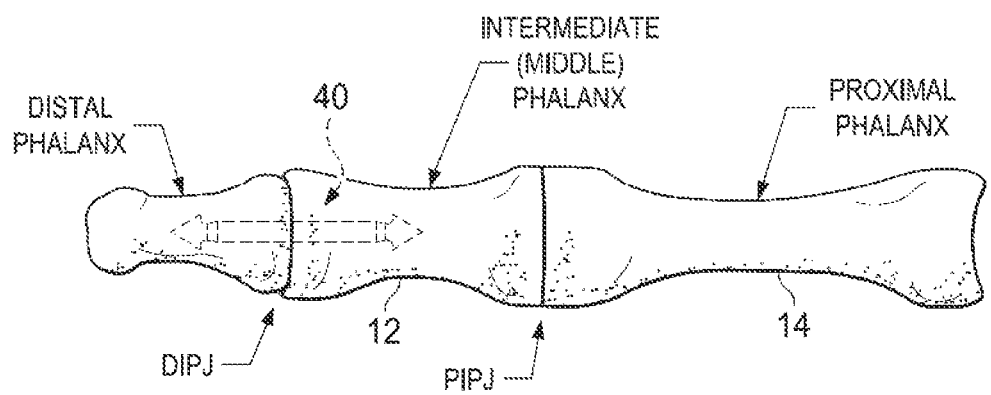
Figure 7:
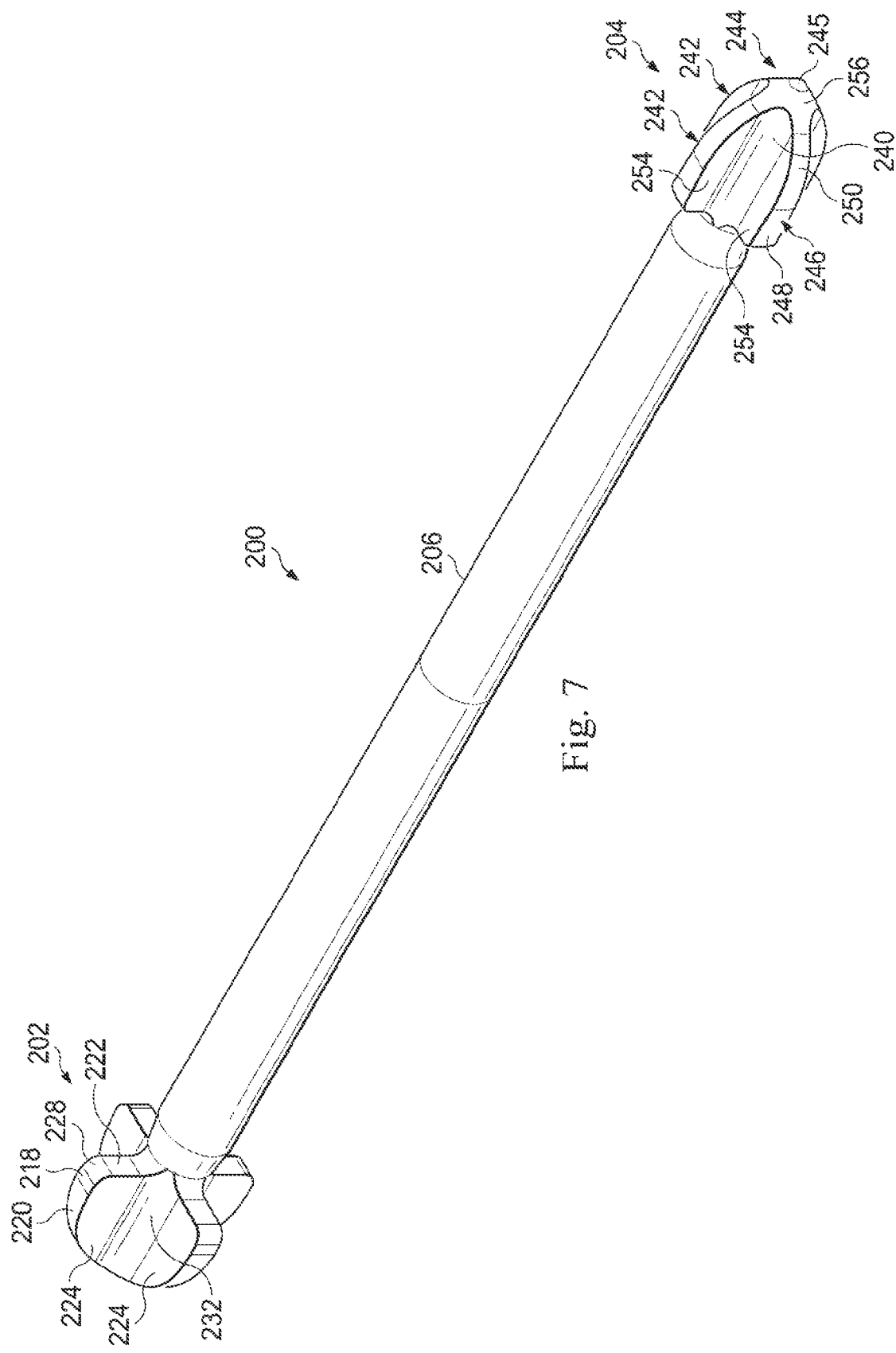

FIG. 1D shows an exemplary device 40 configured and disposed to anchor in the intermediate phalanx and the distal phalanx. The devices described in greater detail herein may form or be used to form any of the devices 100, 20, 30, and 40 shown in FIGS. 1 and 1A-1D, with dimensional changes being a difference between devices. The device 100, as a representative device, is described in detail below.

FIGS. 2-4 show one exemplary embodiment of the device 100 of the present application. The device 100 is designed with a three-dimensionally configured arrow at each end and includes a distal head 102, a proximal head 104, and a body 106 extending between the distal and proximal heads 102, 104. As will become apparent from the below description, the individual components of the device 100 work in conjunction with one another to stabilize bone during arthrodesis procedures and across fractures. While the heads are described as proximal and distal heads, it should be understood that the proximal head may be implanted in a distal position and the distal head may be implanted in a proximal position.

The distal head 102 is formed as a three dimensional arrowhead that is sized for placement in an intramedullary canal of a patient. It is configured so that edges of the arrowhead grasp the cancellous bone in the medullary canal as it is inserted, stabilizing the arthrodesis or fusion site during the osseous union. In this exemplary embodiment, the distal head 102 is formed as a distal end having a distal-most point 108. The distal-most point 108 leads the device 100 down the reamed or broached insertion channel to its final implantation site during insertion. In this example, the distal-most point 108 is a sharp point arranged to glide through tissue within the intramedullary canal to ease insertion. Other configurations of the arrowhead's tip may result in successful insertion based on preparation of the insertion site.

First, second, third, and fourth outer facing surfaces 110, 112, 114, 116 intersect at and extend from the distal most point 108 in the proximal direction, forming a four-sided pyramidal shape. Although shown as having four outer facing surfaces, some embodiments include greater or fewer outer facing side surfaces. In the example shown, opposing surfaces angle away from each other to define a leading angle. For example, the opposing first and third outer facing surfaces 110, 114 define an angle θ relative to a longitudinal axis 117 of the arrowhead shaped distal head 102. In some examples, the angle θ is in the range of about 5 degrees to about 45 degrees. In other examples, the angle θ is in the range of about 7-20 degrees, and in some embodiments, the angle is around 11 degrees. In a similar manner, the opposing second and fourth outer facing surfaces 112, 116 of the arrowhead shaped distal head 102 form an angle α. In the example shown, the angle α is larger than the angle θ. The angle α may be selected to be within the range of about 15-60 degrees, and in some embodiments, is in the range of about 20-45 degrees. In some examples, the angle α is about 30 degrees. The multiple angles described on the distal head may vary based on the size and strength of bone in which the device is to be implanted.

In the embodiment shown, the second and fourth outer facing surfaces 112, 116 have rounded outer surfaces. At the proximal end of these surfaces, the second and fourth outer facing surfaces 112, 116 have a diameter D within a range of about, for example, 2.5-4.5 mm. In some embodiments, the diameter D is in a range of about 3.0-4.0 mm, and in one embodiment, the diameter D is about 3.5 mm. In other embodiments, the second and fourth outer facing surfaces 112, 116 are each planar surfaces.

Because of the different angles between the opposing first and third surfaces 110, 114 and the opposing second and fourth surfaces 112, 116, the width of the distal head 102 differs from side to side. This is easily seen by comparing FIGS. 2 and 3, different views of the distal head 102. This differing width increases resistance to rotation that may occur if the device 100 were cylindrical or to a lesser extent substantially square, although such embodiments are contemplated. Further, the differing width may permit an implanted device to be removed, rotated 90 degrees and implanted again while still providing satisfactory anchoring.

Because of its different widths, the distal head 102 may be sized so that the diameter D of the head 102 is greater than a longitudinal length L of the distal head 102. In embodiments where the second and fourth outer facing surfaces 112, 116 are planar, the distance between the surface measured at the proximal ends of these surfaces correspond to the diameter D measurements mentioned above. The longitudinal length L may be sized in the range of about 1.5-5.5 mm. In one example, the diameter D is around 3.5 mm and the longitudinal length L is about 3 mm. Other sizes however, both larger and smaller, are contemplated, and in one example, the width and the length are substantially equal.

In the example shown, the distal head 102 includes two proximally projecting barbs 118, 120. These barbs are configured to engage tissue within the intramedullary canal and resist movement and migration and/or axial displacement within the canal once they have been inserted into the canal. As can be seen, these barbs 118, 120 are formed by edges of respective outer facing surfaces 112, 116 and because of the pyramidal shape of the distal head, the edges lie in substantially parallel lines.

Inner surfaces of the barbs 118, 120 are formed by first and second undercuts 122, 124 disposed respectively between tips of the barbs 118, 120. These are described in prior U.S. patent application Ser. No. 13/084,048 to Roman, filed Apr. 11, 2011, incorporated herein by reference.

In some embodiments, the barbs are flexible enough to bend if a hard cortical wall is engaged during insertion, providing a reduction in diameter, and enabling additional advancement into an intramedullary canal. In one embodiment, the flexing barbs invoke a change in diameter in the range of about 0.1-0.3 mm. In some examples, the barbs are designed in such a manner that one or both barbs can be trimmed intra-operatively with a straight pin cutter to reduce the diameter of the arrow to fit particularly narrow IM canals. If necessary, the arrowhead tip may be completely removed.

The body 106 extends between and connects the distal head 102 and the proximal head 104. It is a one-piece rigid element structurally configured to withstand loading applied across the joint or fracture being supported. It includes a main body portion 130 and necks 132, 134 at either end leading to the distal and proximal heads 102, 104. As can be seen, the main body portion 130 has a diameter larger than that of the necks 132, 134. The larger body portion 130 may be easier to grasp and secure with a surgical instrument because it has a larger perimeter surface area, while the necks 132, 134 may be sized to permit additional tissue placement and tissue growth immediately adjacent the undercut surfaces 122, 124 of the distal and proximal heads 102, 104. This may result in more secure and lasting anchoring. Thus, this structural arrangement may provide space for extra tissue to grow behind the arrowhead to aid in fixation, while still providing a large gripping surface on the body 106.

Still referring to these figures, the second and fourth outer facing surfaces 112, 116 are angled and intersect with the body 106 at the neck 132. In some examples, the second and fourth outer facing surfaces 112, 114 may smoothly transition to the neck and in other examples; the second and fourth outer facing surfaces 112, 114 meet the neck 132 at an intersecting angle. In some examples, the neck 132 is formed with a rounded perimeter having a diameter substantially similar to the distance between the proximal ends of the second and fourth outer facing surfaces 112, 114.

The second or proximal head 104 is, in the example shown, smaller than the distal head 102, and extends from the body 106 in the opposing direction. For clarity and to reduce duplication, much of the description above applies to the proximal head 104 and is not repeated here with the understanding that the description above applies to the proximal head 104. As such, the proximal head includes four main surfaces forming an arrowhead, labeled as fifth, sixth, seventh, and eighth surfaces. As can be seen, some of these surfaces form an angle β and others form an angle ϕ relative to the longitudinal axis. In one embodiment, the angle β is smaller than the angle θ. In some embodiments, the angle β ranges from about 7-25 degrees, and in one embodiment is 11 degrees. The angle ϕ may be within a range discussed above relative to the angle α, and in one embodiment, is equal to the angle α.

In this embodiment, the proximal head 104 is formed with trailing edge surfaces 140 instead of projecting barbs. The trailing edge surfaces 140 enable bone ingrowth immediately adjacent the trailing edge surfaces, resulting in a relatively quick purchase of the proximal head 104 during healing. The trailing edge surfaces 140 extend substantially perpendicular to the longitudinal axis 117 of the device 100.

The proximal head 104 is sized and configured to be implanted in the subchondral bone at the base of the proximal phalanx. While this proximal head 104 has a smaller diameter and length than the larger distal head 102, because it is implanted in the more dense subchondral bone at the base of the proximal phalanx, the proximal head may achieve a stability and resistance to migratory forces that is similar to that of the larger distal head 102, which is shaped and configured to be inserted in the less dense cancellous bone of the middle phalanx.

In the example shown the distal head 102 has a length that is about 1.5 times the length of the proximal head 104. Likewise, it has an overall width about 1.3-1.5 times the width of the proximal head 104.

Some embodiments of the device include a body having a plantar grade bend. Different embodiments include a bend that may be selected in the range of about 5-25 degrees. In some examples, the bend is selected to be about a 15 degree bend, while yet other embodiments the bend is selected to be about a 10 degree bend, an in another, about a 5 degree bend.

FIGS. 5-9 show another exemplary embodiment of a device, referenced herein as a device 200. The device 200 is designed with a three-dimensionally configured arrow at each end and includes a distal head 202, a proximal head 204, and a body 206 extending between the distal and proximal heads 202, 204 and having a longitudinal axis 207. Features consistent with those described above will not be repeated here for the sake of simplicity, but it is understood that the relevant description of features relative to other embodiments described herein also apply to the device 200.

The distal head 202 includes a central core portion 208 and a plurality of radially extending distal wings 210. The core portion 208 extends along the longitudinal axis 207 of the body 206 and includes the distal end 212. In this example, the distal end 212 is rounded or blunt end to provide smooth insertion into the medullary canal. In addition, because of its rounded shape, when implanted in techniques using bored or reamed holes, the surgeon can feel tactilely when the implant is inserted to the depth of the bored or reamed hole because the rounded end resists further insertion at low insertion forces. However, the surgeon may still insert the device into the intramedullary canal beyond the end of the bored or reamed area by applying additional force. In this embodiment, the distal end 212 is formed of a convexly shaped leading nub 214 extending from the surfaces leading to the wings 210.

The plurality of wings 210 extend radially from the core portion 208 and define the outer shape of the distal head 202. In the embodiment shown, the head 202, as measured from wing to wing, has a diameter sized to fit within an intramedullary canal of a phalanx and more particularly, within a medullary canal of a middle phalanx.

The wings themselves include an outer surface portion 216, a trailing surface portion 222, and lateral sides 224. In the exemplary embodiment shown, the outer surface portion 216 of the wings 210 includes a cylindrical surface portion 218 and a curved leading surface portion 220. The outer perimeter surface portion 218 extends in the longitudinal direction and then intersects with the curved leading surface portion 220. In this example, the outer perimeter surface portion 218 of the plurality of wings 210 together also defines an outer diameter or outer width W1 (FIG. 6) of the distal head 202. In some embodiments, the head has a width sized within the range of about 2.0 mm to 4.5 mm. In one embodiment, the width W1 is sized within the range of about 3.0 mm to 4.0 mm. In one embodiment, the width W1 is sized within the range of about 3.5 mm. In some embodiments, the outer perimeter surface portion 218 of the wings 210 has a curved outer surface that lies along the boundary of a cylindrical shape at the maximum diameter or width W1, as represented by the dashed lines in FIG. 6. Some embodiments are sized to accommodate a particular bone quality and intramedullary canal diameter. For example, for softer bone quality or for larger canals, the diameter of the distal head may be selected to be within a range of 2.5 mm to 5.0 mm.

Extending from the outer perimeter surface portion 218, the wings 210 include the curved leading surface portion 220. The curved leading surface portion 220 faces at least partially in the direction of the distal end 212, and curves from the outer surface portion 216 toward and smoothly intersects with the core portion 208. In some embodiments, the curved leading surface portion 220 has a radius within a range of about 1 mm to 4 mm, and in some embodiments has a radius within a range of about 1.5 mm to 2.5 mm. In one embodiment, the radius is 2 mm.

The trailing surface portion 222 is a surface extending radially inward from the outer surface portion 216 toward the longitudinal axis of the device 200 and intersects with the core portion 208. In the embodiment shown, the trailing surface portion 222 has a surface that lies substantially normal to the longitudinal axis 207, although in other embodiments, it may be angled obliquely relative to the longitudinal axis. A rounded, distally projecting edge 228 connects the trailing surface portion 222 to the outer perimeter surface portion 218 of the outer surface portion 216.

In the embodiment shown, each wing 210 includes two lateral sides 224. In the example shown, the lateral sides extend from the outer surface portion 216 to the core portion 208. Depending on the embodiment, these lateral sides 224 may be formed in parallel planes or may be wedge-shaped. The thickness of the wing 210 is defined by the distance between the lateral sides 224 and the pull-out resistance is determined by the thickness of the wing 210 at the trailing surface portion. A wing 210 having lateral sides 224 in parallel planes will have uniform thickness and may be easier to implant while still providing rotational stability. In other embodiments however, these lateral sides 224 may be formed of nonparallel planes and may form a wedge-shape. For example, one embodiment includes a wing 10 having a leading portion having a thickness about 0.38 mm at the leading end and a thickness of about 0.52 mm at the trailing end. Other angles and dimensions are also contemplated. Accordingly, the wings are thinner toward the leading end than the trailing end. Embodiments with wedge-shaped wings may require more force to implant. However, they may also provide closer contact between the bone and the wing 210 because the wing may become gradually thicker from the leading edge to the trailing edge. In addition, increasing thickness of the wing toward the trailing edge maximizes the resistance to pull-out because the wing at the trailing surface portion is at its thickest location.

In some embodiments, the lateral sides 224 are nonplanar and have a curved surface that promotes interference with bone tissue to resist migration and rotation. Some embodiments include wings that vary by wing thickness. For example, some embodiments include two wings having a first thickness and two additional wings having a second thickness greater than the first thickness. The core portion 208 smoothly connects and spans between adjacent wings with a cylindrical surface 232 that extends the length of the wings 210.

Because the distal end 212 has a smooth bullet-nose shape, the likelihood of the distal end catching on the cortex and preventing the implant from being advanced smoothly may be diminished. During insertion, the wings 210 act as sled runners to help the device 200 slide easily down a reamed pilot hole. In addition, the smooth and curved leading surface portion 220 on the wings 210 may enable the implant to be self-centering during the insertion process.

While the distal head 202 is shown having four wings 210 forming a plus or cruciate configuration, other embodiments include a different number of wings. One embodiment includes three wings, while another embodiment includes two wings. Yet other embodiments include more than four wings. Depending on the embodiment, the distal head 202 may comprise between three and eight distal wings 210 arranged in a symmetric or asymmetric manner. Some examples have distal wings forming a cruciate or plus shape, an X shape, a five-sided star shape, or a six-sided star shape, or a four-wind dorsally (like an underlined V), among other possible combinations. The number of wings may affect the pull-out resistance of the device 200. For example, a balance between the number of wings and their relative size may permit the device to be designed to achieve a desired pull-out resistance. Reducing the diameter of the wings may permit the device 200 to be implanted within smaller diameter intramedullary canals while still providing suitable resistance to pull-out. Some embodiments have the wings of the proximal head rotatably offset from the wings of the distal head. For example, while the wings on the distal head may be disposed at 3, 6, 9, and 12 o'clock, the wings on the proximal head may be disposed at 2, 5, 8, and 11 o'clock. In some embodiments, the wings are offset by 45 degrees.

Because of the central core portion 208 design, the pilot hole preparation may be done with a rotary motion, such as a power or manual reamer or drill, thereby possibly reducing the need for the step of broaching the pilot hole to form a rectangular cavity. Some embodiments include a head length that is minimized in order to permit as much bone growth behind the trailing surface portion possible to contribute to resistance to pull-out. In one embodiment, the length of the distal head is within the range of about 2.0 mm to 3.0 mm. Other sizes are also contemplated.

The blade orientation for the distal head 202 provides not only resistance to rotation and pull-out but also may ease pulling the middle phalanx over the distal head 202 as it the portion of the device that protrudes from the proximal phalange during insertion.

The proximal head 204 includes a central core portion 240 and a plurality of radially extending wings 242. Many features of the proximal head 204 are similar to that of the distal head 202 and not all the features are re-described here, recognizing that one of ordinary skill would understand that features and alternatives described relative to the distal head 202 have equal applicability to the proximal head 204. Like the core portion 208 of the distal head 202, the central core portion 240 extends along the longitudinal axis 207 of the body 206. The core portion 240 includes a proximal end 244. In this example, the core portion 240 and the proximal end 244 differs in shape as described below, while still maintaining a rounded or blunt end to provide smooth insertion into the medullary canal. In this embodiment, the core portion proximal end 244 includes a conical surface portion 256 that connects the leading surface portion 250 and includes a convexly shaped leading nub 245 extending from the surfaces leading to the wings 242.

The plurality of wings 242 extend radially from the core portion 240 and define the outer shape of the proximal head 204. In the embodiment shown, the head 202, as measured from wing to wing, has a diameter sized to fit within an intramedullary canal of a phalanx and more particularly, within a canal of a proximal phalanx.

The wings 242 themselves include an outer surface portion 246, a trailing surface portion 252, and lateral sides 254. In the exemplary embodiment shown, the outer surface portion 246 of the wings 242 includes an outer perimeter surface portion 248 and a curved leading surface portion 250. The outer perimeter surface portion 248 extends in the longitudinal direction and then intersects with the curved leading surface portion 250. In this example, the outer perimeter surface portion 248 of the plurality of wings 242 together also defines an outer diameter or outer width W2 (FIG. 9) of the distal head 202. In some embodiments, the proximal head 204 has a width sized within the range of about 1.0 mm to 3.5 mm. In one embodiment, the width W2 is sized within the range of about 2.0 mm to 3.0 mm. In one embodiment, the width W2 is sized within the range of about 2.5 mm. In some embodiments, the outer perimeter surface portion 248 of the wings 242 has a curved outer surface that lies along the boundary of a cylindrical shape at the maximum diameter or width W2, as represented by the dashed lines in FIG. 9.

Extending from the outer perimeter surface portion 248, the wings 242 include the curved leading surface portion 250. The curved leading surface portion 250 curves from the outer surface portion 216 toward and smoothly intersecting with the conical surface portion 256 of the core portion 208. In some embodiments, the curved leading surface portion 250 has a radius sized in the ranges as described with reference to the curved leading surface portion 220. In one embodiment, the covered leading surface portions 220, 250 have the same radius.

The trailing surface portion 252 extends radially inward from the outer surface portion 246 toward the longitudinal axis of the device 200 and intersects with the core portion 240. A rounded edge 258 connects the trailing surface portion 252 to the outer perimeter surface portion 248 of the outer surface portion 246.

Each wing 242 includes two lateral sides 254. In one embodiment, the thickness of the wings 242 is measured between the lateral sides 254 and is in the range of 0.020 mm and 0.060 mm. In one embodiment, the wings are wedge shaped and taper from a thickness of 0.37 mm at its leading end to 0.053 at its trailing end.

As indicated above, the overall length of the proximal head 204 is greater than that of the distal head 202. However, the length can be shortened to enhance pull-out resistance. For example, the resistance to pull-out may increase as the distance from the trailing surface portion of the distal or proximal head to the osteotomy increases. For the distal head 202 that is implanted in the middle phalanx, a shorter head may offer resistance to rotation and still increase the distance from the trailing surface portion of the implant wings to the osteotomy site when implanted to the same depth. Because the trailing surface portion of the wing on the shorter head is farther from the fracture site, a radiograph would give the appearance of the device being more deeply implanted in the middle phalanx. As such the distal head 202 with its larger diameter is intended for implantation in the medial phalanx and the proximal head 204 with its smaller diameter is intended for implantation in the proximal phalanx.

The body 206 is a rigid shaft extending between and connecting the distal head 202 and the proximal head 204. In the embodiment shown, the body 206 is cylindrically shaped and has a substantially smooth exterior surface. In one embodiment, the body 206 has a diameter or a cross-sectional thickness within a range of about 1.2 mm to 2.0 mm. In one embodiment, the body 206 has a diameter or a cross-sectional thickness of about 1.6 mm. Other sizes, larger and smaller are contemplated. The body 206 includes a necked-down region adjacent the proximal and distal head as the body merges with the central core portion.

In some embodiments, the proximal and distal heads form about a 30% or less of the overall length of the device. In one example, the distal head has a length of about 2.5 mm, the proximal head has a length of about 3.0 mm, and the body has a length about 13.5 mm or greater.

In the embodiment shown, the body 206 has a substantially constant diameter. However some embodiments have body diameters that vary along the length of the body 206 to correspond to forces and to increase the area of the arrow-head tip resisting pull-out and rotational forces. Two such embodiments are described below relative to FIGS. 10 and 11.

FIG. 10 shows another embodiment of a device referenced herein by the numeral 300. The device 300 includes a distal head 302, a proximal head 304, and a body 306. The distal and proximal heads 302, 304 include features similar to those described above, and the descriptions apply to this embodiment, recognizing that the size ratio of the different heads may differ on the device 300. Here, the proximal head 304 include a core portion 308 and wings 310. The body 306 in this embodiment includes a tapered shaft region 312 that extends along a substantial portion of the body 306.

In this embodiment, the size ratio of tapered shaft region 312 to the adjacent core portion 308 of the head may be selected to be minimized. This may permit the body 306 to be deeply embedded within the phalanx with a minimal amount of tissue disruption. Some embodiments have less than a 1:1.5 tapered shaft region to core portion size ratio, while other embodiments have a 1:1 size ratio. Other sizes and ratios are contemplated. The reduced diameter of the tapered shaft region 308 may extend less than half the distance of the body 306 so that the thicker region of the body 306 may be disposed at the fusion region when the device 200 is implanted. In the exemplary embodiment shown, the tapered shaft region 312 extends for a length of more than about 15% of the length of the entire body. In one embodiment, the tapered shaft region 312 extends from the proximal head a distance between about 15% and 45% of the length of the body 306. In some examples, the tapered shaft region 312 extends a distance within a range of about 20% and 30% of the length of the body 306. This may provide a suitable region for bone ingrowth behind the proximal head 304, while still having the thicker portion of the body at the osteotomy site. While referred to as a tapered shaft region 312, the narrow region of the shaft may also be cylindrical, and may be referred to as a narrow region.

This also may permit the proximal head 304 to be embedded in the subchondral bone of the proximal phalanx. Reducing the ratio of the core portion 308 to the body 306 may increase the resistance to rotation and pull-out. In one embodiment, the body diameter or width is set at a diameter of 1.0 mm so that an additional 0.25 mm per wing (0.5 mm total) is available to resist rotational forces. The increased area resisting pull-out is also 0.25 mm per wing multiplied by the width of the wing 310 at the trailing surface portion, multiplied by the number of wings 310. In this embodiment, a reamer width would be reduced to the width of the body 306 at the narrowest point.

In the example shown, the thickness or cross-sectional width of the body 306 that aligns with the osteotomy site and into the distal tip of the implant would remain at the thickest portion of the body 306, which in one embodiment, is 1.6 mm.

FIG. 11 shows another embodiment of a device, reference herein by the numeral 400. The device 400 includes a distal head 402, a proximal head 404, and a body 406. The distal and proximal heads 402, 404 include features similar to those described above, and the descriptions apply to this embodiment, recognizing that the size ratio of the different heads may differ on the device 400. In this embodiment, the body 406 includes a central region 410 of increased thickness. Accordingly, the body 406 includes narrower regions 412 at the distal and proximal ends, and these narrow further at necks 414 to form the respective distal and proximal heads 402, 404.

Here, the central region 410 may provide greater strength and a tighter fit at the site of the osteotomy. In one embodiment, the width or diameter of the body 106 in the central region 410 is within a range of about 1.8 mm-2.2 mm to enhance the fixation at the osteotomy site and to stabilize the device by helping to reduce play of the device 200. This may also increase the strength of an already strong implant at the point of greatest potential stresses. In such an embodiment, the reamer diameter may remain at a size to accommodate the narrower regions 412. For example, the narrow regions 412 may have a diameter of about 1.6 mm, and therefore, in some examples, the reamer diameter would also be 1.6 mm. In one embodiment, the central region 410 may extend about 40-70% of the length of the body. In other embodiments, the central region extends about 40-60% of the length of the body.

Figure 8:
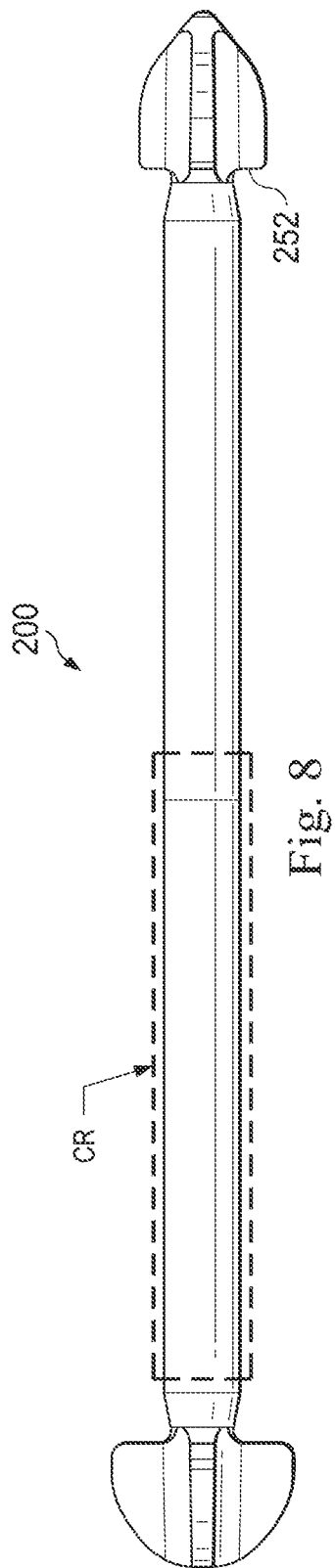
Figure 9:
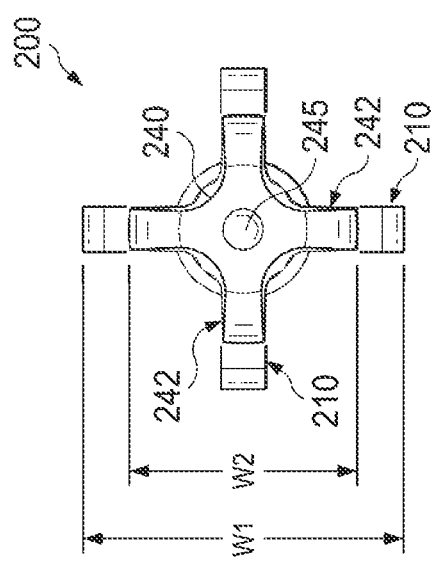
Figure 15:
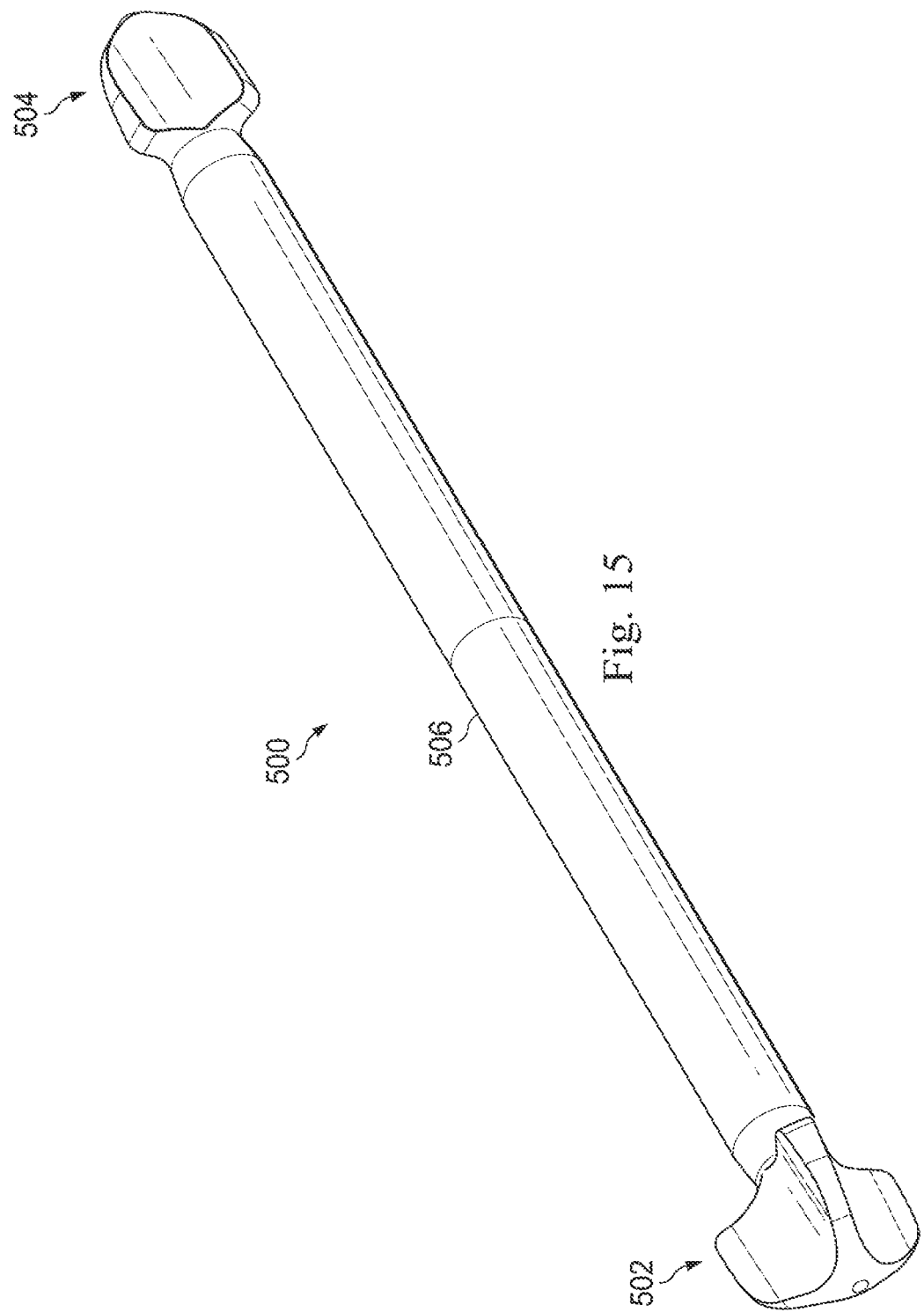
Figure 16:
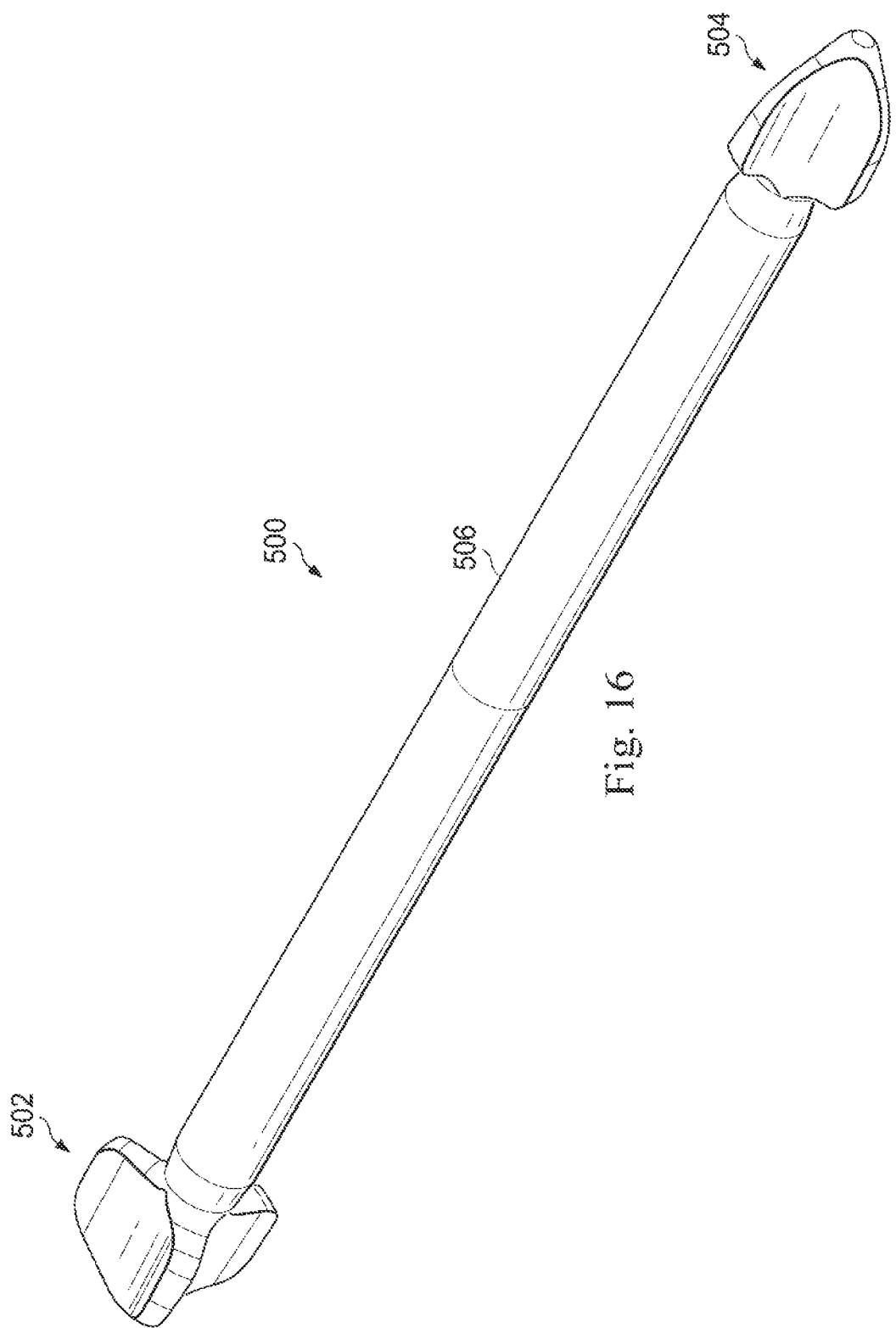

Some embodiments of the bodies disclosed herein include a coating or tissue growth material. For example, some embodiments include an aggressive porous material or coating that is "sticky" to tissue. Some examples include a bone-growth promoting substance, such as, for example, a hydroxyapatite coating formed of calcium phosphate, tricalcium phosphate (TCP), and/or calcium carbonate. Alternatively, osteoinductive coatings, such as proteins from transforming growth factor (TGF) beta superfamily, or bone-morphogenic proteins, such as BMP2 or BMP7, may be used. These coatings may increase adhesion to cancellous bone, increasing resistance to pull-out and rotational forces. They also may accelerate bony ingrowth and accelerate consolidation of the bone. The coating may be applied along the entire body of the device, or may be applied only along a specific region, such as a region, such as the half of the body adjacent the distal head, for example. FIG. 8 shows one example of a coating region, identified by the box labeled CR. The coating may be arranged in other ways also.

Although shown as cylindrical, any of the bodies disclosed herein may have a cross-section of any suitable shape, and may include, for example, a shaft shape that is triangular shaped, square shaped or one with edges rather than cylindrical. These types of body cross-sections can provide additional resistance to rotational forces. In another example, edges emerging from the body can serve to provide additional fixation.

In some embodiments, the proximal head 204 is sized and configured to be embedded in the subchondral bone at the base of the proximal phalanx. The rounded blunt tip may require greater force than the sharper, pointier arrow of earlier devices to progress farther into the subchondral bone than the prepared hole provides. Accordingly, the blunt bullet nose may prevent the implant from advancing past the end of the reamed pilot hole.

In one embodiment, the length of the proximal head is about 2.0 mm in the longitudinal direction. This length permits the addition of one or two additional wings that may increase both the level of the resistance to rotation and pull-out without increasing the length of the arrowhead. Increasing the length could adversely affect the pull-out resistance in vivo, for example, if the longer arrowhead were to not be completely embedded in subchondral bone. In this example, the wings are formed so that the head is substantially symmetrical. In other examples however, the proximal head comprises between three and eight proximal wings arranged in a symmetric or asymmetric manner. Some examples have proximal wings forming a cruciate or plus shape, an X shape, a five-sided star shape, or a six-sided star shape, or a four-wind dorsally (like an underlined V), among other possible combinations.

FIGS. 12-16 show an additional embodiment of a device, referenced herein by the numeral 500, including a distal head 502, a proximal head 504, and a body 506. The distal and proximal heads 502, 504 include features similar to those described above, and the descriptions apply to this embodiment, recognizing that the size ratio of the different heads may differ on the device 500. In this embodiment, the distal and proximal head each include three wings radially extending from a central core. As can be seen, and consistent with the description above, the distal head has a greater width and a smaller length than the proximal head. Here, as can be seen in the end views shown in FIGS. 13 and 14, the wings of the distal head and the proximal head are rotationally offset. Since there are three wings, they are rotationally offset by 60 degrees.

The devices may be implanted using any of a number of surgical instruments or tools, including for example, a reamer, a broach, and an insertion forceps. These instruments are described in detail in prior U.S. patent application Ser. No. 13/084,048 to Roman, filed Apr. 11, 2011, and incorporated herein by reference.

Furthermore, the devices disclosed herein may be provided as a kit in combination with a plurality of devices of different sizes or the instruments themselves. One exemplary kit includes a device as described above, with the reamer, the broach, and the insertion forceps. Other kits are described in prior U.S. patent application Ser. No. 13/084, 048 to Roman, filed Apr. 11, 2011, and incorporated herein by reference.

The devices herein may be used in exemplary surgical methods for implanting the device for the treatment or correction of bone deformities. When implanted, the arrowhead configuration of both the distal and proximal heads captures bone on both sides of the fusion or fracture site, and may provide internal stability. This is accomplished by pressing and locking the distal and proximal heads into the surrounding bone. The body of the device extends from each head (proximal and distal) and is the portion of the implant that crosses or spans the fusion or fracture site.

It should be noted that the exemplary devices described herein may be used for treatments such as hammertoe, and in some examples, may be used to treat conditions in the fingers of a hand, or alternatively may be used to treat bone fractures. FIG. 17 is one example showing an example device, which could be any of the devices disclosed herein implanted within phalanges of the hand. In addition, removal of the device may be relatively easier than prior, conventional devices. For example, to remove the device, the cylindrical main body may be first cut, and then a cannulated drill may be fit over the cylindrical main body and drilled over to remove bony on-growth from the cylindrical body so that the arrowhead tip can be removed without tearing the bone. This may prevent the health care provider from having to cut the cortical bone in order to remove the implant. Accordingly, the cylindrical shape of the main body may help reduce a chance of compromising cortical bone during revision surgeries. Uses of the device may include but are not limited to hand surgery, orthopedic surgery, plastic surgery, and podiatric surgery. In addition, the implant may be inserted in a variety of angles that differ from its intended position in medullary bone. In some examples, the implant may also be placed through cortical bone and tendon of the hand or foot.

In some examples, the device is machined from a single piece of 316L stainless steel, making it a weld-less, single monolith structure. In other embodiment, it may be formed of two structures welded or brazed together, as shown in the cross-sectional view in FIG. 4. Various lengths may be provided to meet patient sizing restrictions. The overall lengths of the device may be in the range of 10 mm to 40 mm, while some lengths are within the range of 15 mm to 25 mm. When the device is formed of a single piece of metal, potential stress-risers occurring from welds or adhesives are eliminated and there is no need to assemble intra-operatively. Further, the material and size are selected so that the device has bending and fatigue characteristics able to endure the forces exerted on the lesser toes.

In some examples, the arrowheads may be reconfigured at different positions to one another and may obtain the same stability to the arthrodesis/fracture site. For example, some embodiments have a proximal arrow vertical to the shaft or a distal arrow horizontal to the shaft. The same can be said for different angle increments to each arrow.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

We claim:

1. An intramedullary fixation device used in bone fixation and stabilization, comprising:
   an arrowhead-shaped distal head comprising a distal end having a distal tip, the distal head having first, second, third, and fourth outwardly facing side surfaces forming a pyramidal shape, the first and third side surfaces being opposed from each other and forming a first angle, and the second and fourth side surfaces being opposed from each other and forming a second angle, the second angle being different than the first angle, each of the first and third side surfaces having a proximally projecting edge forming a tip of a barb, the barbs being configured to engage tissue and inhibit rotational movement and inhibit axial movement of the distal head in a proximal direction, the barbs comprising first trailing edge surfaces extending from the tips in a direction substantially perpendicular to a longitudinal direction of the distal head and intersecting with undercut surfaces, the undercut surfaces extending from the first trailing edge surfaces distally and to a first neck region, the undercut surfaces having a distal depth such that the first trailing edge surfaces of the barbs are disposed proximal of the undercut surfaces, the distal head having a first dimensional width measured between proximally projecting edges of the first and third side surfaces;
   an arrowhead-shaped proximal head comprising a proximal end having a proximal tip, the proximal head having fifth, sixth, seventh, and eighth outwardly facing side surfaces, the fifth and seventh side surfaces being opposed from each other and forming a third angle, and the sixth and eighth side surfaces being opposed from each other and forming a fourth angle, the third angle being different than the fourth angle, each of the fifth and seventh side surfaces having a distally projecting edge, the proximal head comprising a second trailing edge surface intersecting the distally projecting edge of the fifth and seventh side surfaces, the second trailing edge surface extending in a direction substantially perpendicular to a longitudinal direction of the proximal head and intersecting with a second neck region, the proximal head having a second dimensional width measured between distally projecting edges of the fifth and seventh side surfaces, the first dimensional width being within the range of about 1.3-1.5 times the second dimensional width; and a rigid body extending between and connecting the distal head and the proximal head, the rigid body having the first and second neck regions joined to the undercut surfaces of the distal head and the second trailing edge surface of the proximal head, respectively, in a manner such that the first and second trailing edge surfaces are perpendicular to a longitudinal axis of the body, the body having a rigidity sufficient to withstand bending loading applied by the phalanges.

2. The intramedullary fixation device of claim 1, wherein the first angle is smaller than the third angle.

3. The intramedullary fixation device of claim 1, wherein the first angle is smaller than the second angle and the third angle is smaller than the fourth angle.

4. The intramedullary fixation device of claim 1, wherein the second and fourth side surfaces include proximal ends that relatively smoothly transition to the body.

5. The intramedullary fixation device of claim 1, wherein the body comprises a main portion, the first neck portion, and the second neck portion, the first and second neck portions having a cross-sectional area smaller than a cross-section area of the main portion.

* * * * *